US00PP25400P2

(12) United States Plant Patent
Isobe

(10) Patent No.: US PP25,400 P2
(45) Date of Patent: Mar. 31, 2015

(54) ***PETUNIA* PLANT NAMED 'SUNSURF KITATSU'**

(50) Latin Name: *Petunia×hybrida*
Varietal Denomination: Sunsurf Kitatsu

(71) Applicant: Yasuko Isobe, Shiga (JP)

(72) Inventor: Yasuko Isobe, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 190 days.

(21) Appl. No.: 13/815,130

(22) Filed: Jan. 31, 2013

(51) Int. Cl.
*A01H 5/00* (2006.01)

(52) U.S. Cl.
USPC ..... Plt./356.1

(58) Field of Classification Search
USPC ..... Plt./356.1
See application file for complete search history.

*Primary Examiner* — June Hwu
*Assistant Examiner* — Louanne Krawczewicz Myer
(74) *Attorney, Agent, or Firm* — C. A. Whealy

(57) ABSTRACT

A new and distinct cultivar of *Petunia* plant named 'Sunsurf Kitatsu', characterized by its compact, mounding and trailing plant habit; vigorous growth habit; freely branching habit; freely flowering habit; long flowering period; large pale yellow green-colored flowers with darker yellow green-colored venation; and good garden performance.

1 Drawing Sheet

Botanical designation: *Petunia×hybrida*.
Cultivar denomination: 'SUNSURF KITATSU'.

BACKGROUND OF THE INVENTION

The present invention relates to a new and distinct cultivar of *Petunia* plant, botanically known as *Petunia×hybrida* and hereinafter referred to by the name 'Sunsurf Kitatsu'.

The new *Petunia* plant is a product of a planned breeding program conducted by the Inventor in Higashiomi, Shiga, Japan. The objective of the breeding program is to create new freely branching and freely flowering *Petunia* plants with a compact, mounding and trailing plant habit and numerous large attractive flowers.

The new *Petunia* plant originated from a cross-pollination made by the Inventor in July, 2007 in Higashiomi, Shiga, Japan of a proprietary selection of *Petunia×hybrida* identified as code number Px1634-02, not patented, as the female, or seed, parent with a proprietary selection of *Petunia×hybrida* identified as code number Pf919-02, not patented, as the male, or pollen, parent. The new *Petunia* plant was discovered and selected by the Inventor as a single flowering plant within the progeny of the stated cross-pollination in a controlled greenhouse environment in Higashiomi, Shiga, Japan in June, 2008.

Asexual reproduction of the new *Petunia* plant by terminal cuttings in a controlled greenhouse environment in Higashiomi, Shiga, Japan since June, 2008 has shown that the unique features of this new *Petunia* plant are stable and reproduced true to type in successive generations.

SUMMARY OF THE INVENTION

Plants of the new *Petunia* have not been observed under all possible environmental conditions and cultural conditions. The phenotype may vary somewhat with variations in environmental conditions such as temperature and light intensity without, however, any variance in genotype.

The following traits have been repeatedly observed and are determined to be the unique characteristics of 'Sunsurf Kitatsu'. These characteristics in combination distinguish 'Sunsurf Kitatsu' as a new and distinct *Petunia* plant:

1. Compact, mounding and trailing plant habit.
2. Vigorous growth habit.
3. Freely branching habit.
4. Freely flowering habit.
5. Long flowering period.
6. Large pale yellow green-colored flowers with darker yellow green-colored venation.
7. Good garden performance.

Plants of the new *Petunia* can be compared to plants of the female parent selection. Plants of the new *Petunia* differ primarily from plants of the female parent selection in the following characteristics:

1. Plants of the new *Petunia* are more compact than plants of the female parent selection.
2. Plants of the new *Petunia* are more mounding than plants of the female parent selection.
3. Plants of the new *Petunia* and the female parent selection differ in flower color as plants of the female parent selection have light yellow-colored flowers.

Plants of the new *Petunia* can be compared to plants of the male parent selection. Plants of the new *Petunia* differ primarily from plants of the male parent selection in the following characteristics:

1. Plants of the new *Petunia* are broader than plants of the male parent selection.
2. Plants of the new *Petunia* are more trailing than plants of the male parent selection.
3. Plants of the new *Petunia* and the male parent selection differ in flower petal shape as plants of the male parent selection have flower petals with obtuse-shaped apices.

Plants of the new *Petunia* can also be compared to plants of the *Petunia* 'Sunsurf Kiusa', disclosed in U.S. Plant Pat. No. 24,594. In side-by-side comparisons conducted in Higashiomi, Shiga, Japan, plants of the new *Petunia* and 'SunsurfKiusa' differed primarily in the following characteristics:

1. Plants of the new *Petunia* were taller and broader than plants of 'Sunsurf Kiusa'.
2. Plants of the new *Petunia* had smaller leaves than plants of 'Sunsurf Kiusa'.
3. Plants of the new *Petunia* are more freely flowering than plants of 'Sunsurf Kiusa'.
4. Plants of the new *Petunia* and 'Sunsurf Kiusa' differed slightly in flower color.
5. Plants of the new *Petunia* and 'Sunsurf Kiusa' differed in flower petal shape as plants of 'Sunsurf Kiusa' had flower petals with mucronate-shaped apices.
6. Plants of the new *Petunia* had longer peduncles than plants of 'Sunsurf Kiusa'.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the top of the sheet comprises a side perspective view of a typical flowering plant of 'Sunsurf Kitatsu' grown in a container.

The photograph at the bottom of the sheet is a close-up view of a typical flowering plant of 'Sunsurf Kitatsu'.

DETAILED BOTANICAL DESCRIPTION

The aforementioned photographs and following observations, measurements and values describe plants grown during the summer in 15-cm containers in an outdoor nursery in Higashiomi, Shiga, Japan and under cultural practices typical of commercial *Petunia* production. During the production of the plants, day temperatures averaged 23° C. and night temperatures averaged 13° C. Plants were four months old when the photographs and the description were taken. In the following description, color references are made to The Royal Horticultural Society Colour Chart, 2007 Edition, except where general terms of ordinary dictionary significance are used.

Botanical classification: *Petunia×hybrida* 'Sunsurf Kitatsu'.

Parentage:

*Female, or seed, parent*.—Proprietary selection of *Petunia×hybrida* identified as code number Px1634-02, not patented.

*Male, or pollen, parent*.—Proprietary selection of *Petunia×hybrida* identified as code number Pf919-02, not patented.

Propagation:

*Type*.—By terminal cuttings.

*Time to initiate roots, summer and winter*.—About one week at temperatures of about 15° C. to 20° C.

*Time to produce a rooted young plant, summer and winter*.—About three weeks at temperatures of about 15° C. to 20° C.

*Root description*.—Fibrous; white in color.

*Rooting habit*.—Freely branching; dense.

Plant description:

*Plant form and growth habit*.—Compact, mounding and trailing plant habit; freely branching habit with numerous lateral branches developing per plant; pinching enhances lateral branch development; vigorous growth habit.

*Plant height*.—About 23 cm.

*Plant diameter*.—About 58.9 cm.

Lateral branch description:

*Length*.—About 22.7 cm.

*Diameter*.—About 2.1 mm.

*Internode length*.—About 1.9 cm.

*Strength*.—Strong, flexible.

*Aspect*.—Upright to outwardly.

*Texture*.—Pubescent.

*Color*.—Close to 144A.

Foliage description:

*Arrangement*.—Alternate, simple.

*Length*.—About 2.7 cm.

*Width*.—About 1.3 cm.

*Shape*.—Ovate.

*Apex*.—Obtuse.

*Base*.—Attenuate.

*Margin*.—Entire.

*Texture, upper and lower surfaces*.—Sparsely pubescent.

*Venation pattern*.—Pinnate; reticulate.

*Color*.—Developing and fully expanded leaves, upper surface: Close to 138A; venation, close to 144B. Developing and fully expanded leaves, lower surface: Close to 138B; venation, close to N144C.

*Petioles*.—Length: About 4.7 mm. Diameter: About 1.3 mm. Texture, upper and lower surfaces: Pubescent. Color, upper and lower surfaces: Close to 144A.

Flower description:

*Flower arrangement and habit*.—Single salverform flowers arising from upper leaf axils; freely flowering habit with usually about 48 flowers developing per plant; flowers face upright to outwardly.

*Fragrance*.—None detected.

*Natural flowering season*.—Early flowering habit, plants of the new *Petunia* initiate and develop flowers about three to four weeks after planting; long flowering period, flowering commences naturally during the spring and plants flower continuously throughout the summer until late autumn in Japan.

*Flower longevity*.—Individual flowers last about seven to ten days on the plant; flowers not persistent.

*Flower diameter*.—About 5.5 cm.

*Flower length (depth)*.—About 5 cm.

*Throat diameter*.—About 1.1 cm.

*Tube diameter, base*.—About 2.7 mm.

*Tube length*.—About 3.25 cm.

*Flower buds*.—Length: About 4.4 cm. Diameter: About 1 cm. Shape: Cylindrical. Color: Close to 150D.

*Corolla*.—Arrangement: Five petals fused at the base and opening into a flared trumpet. Petal length from throat: About 2.1 cm. Petal width: About 2.4 cm. Petal shape: Spatulate. Petal apex: Cuspidate, sinuate. Petal margin: Entire, undulate. Petal texture, upper surface: Smooth, glabrous. Petal texture, lower surface: Smooth, glabrous. Throat texture: Smooth, glabrous. Tube texture: Smooth, glabrous. Color: Petal, when opening, upper and lower surfaces: Close to 150D; venation, close to 150A. Petal, fully opened, upper and lower surfaces: Close to 150D; venation, close to 150A. Throat: Close to 3A; venation, close to 3A. Tube: Close to 149D; venation, close to 149C.

*Calyx*.—Arrangement: One star-shaped calyx tube with five sepals in a single whorl and fused at the base. Sepal length: About 1.1 cm. Sepal width: About 3.1 mm. Sepal shape: Narrowly elliptic. Sepal apex: Obtuse, narrow. Sepal margin: Entire. Sepal texture, upper and lower surfaces: Pubescent. Color: Developing and fully developed sepals, upper surface: Close to 138A. Developing and fully developed sepals, lower surface: Close to 139C; towards the base, close to N144D.

*Peduncles*.—Length: About 2 cm. Diameter: About 1.9 mm. Strength: Strong. Aspect: Semi-upright. Texture: Pubescent. Color: Close to 143C.

*Reproductive organs*.—Stamens: Quantity per flower: Five. Stamen length: About 2.1 cm to 2.5 cm. Anther shape: Ellipsoidal. Anther size: About 2 mm by 2.4 mm. Anther color: Close to 3D. Pollen amount: Abundant. Pollen color: Close to 11B. Pistils: Quantity per flower: One. Pistil length: About 2.4 cm. Style color: Close to 144D. Stigma shape: Transversely ellipsoidal. Stigma color: Close to 144B. Ovary color: Close to 144C. Seeds and fruits: Seed and fruit development have not been observed on plants of the new *Petunia*.

Garden performance: Plants of the new *Petunia* have been observed to have good garden performance and to tolerate rain, wind and temperatures ranging from about 5° C. to about 35° C.

Pathogen & pest resistance: Plants of the new *Petunia* have not been observed to be resistant to pathogens and pests common to *Petunia* plants.

It is claimed:

1. A new and distinct *Petunia* plant named 'Sunsurf Kitatsu' as illustrated and described.

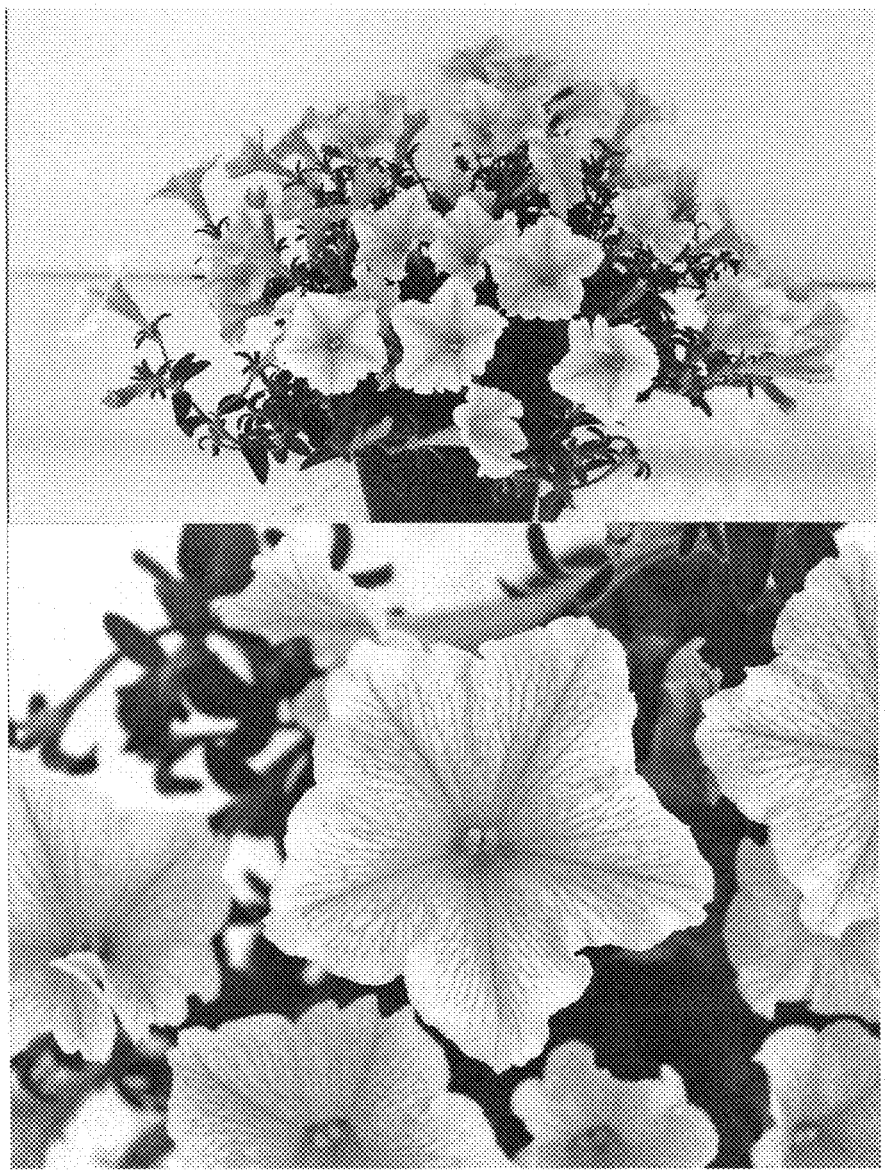

* * * * *